United States Patent [19]

Sherman

[11] Patent Number: 5,322,667

[45] Date of Patent: * Jun. 21, 1994

[54] PRESERVATIVE SYSTEM FOR OPHTHALMIC AND CONTACT LENS SOLUTIONS AND METHOD FOR CLEANING DISINFECTING AND STORING CONTACT LENSES

[75] Inventor: Guy J. Sherman, Mandeville, La.

[73] Assignee: Sherman Pharmaceuticals, Inc., Mandeville, La.

[*] Notice: The portion of the term of this patent subsequent to Aug. 25, 2009 has been disclaimed.

[21] Appl. No.: 930,787

[22] Filed: Aug. 17, 1992

Related U.S. Application Data

[63] Continuation-in-part of Ser. No. 551,514, Jul. 11, 1990, Pat. No. 5,141,665, which is a continuation of Ser. No. 242,410, Sep. 8, 1988, abandoned, which is a continuation-in-part of Ser. No. 140,075, Dec. 31, 1987, abandoned, which is a continuation-in-part of Ser. No. 32,891, Mar. 31, 1987, abandoned.

[51] Int. Cl.$^5$ .................. A01N 25/02; C11D 3/48
[52] U.S. Cl. .................. 422/28; 514/840; 252/106
[58] Field of Search .......... 514/839, 840, 496; 252/547, DIG. 5, DIG. 7, 106; 422/28

[56] References Cited

U.S. PATENT DOCUMENTS

| | | | |
|---|---|---|---|
| 3,954,965 | 5/1976 | Boghosian et al. | 514/496 X |
| 4,406,706 | 9/1977 | Krezanoski | 252/DIG. 7 X |
| 4,443,429 | 4/1984 | Smith et al. | 514/839 X |
| 4,543,200 | 9/1985 | Sherman | 252/106 |
| 4,560,491 | 12/1985 | Sherman | 252/106 |
| 5,141,665 | 8/1992 | Sherman | 252/106 |

OTHER PUBLICATIONS

W. H. Coles, *Effects Of Antibiotics On The In Vitro Rabbit Corneal Endothelium*, 14 Investigative Ophthalmology 246-250 (Mar. 1975).

Gerald L. Feldman, *Benzyl Alcohol –New Life as an Ophthalmic Preservative*, Spectrum (May 1989).

Gerald L. Feldman, *A New System For RGP Lens Care*, Contact Lens Forum Jun. 1989.

Primary Examiner—Robert J. Warden
Assistant Examiner—E. Leigh Dawson
Attorney, Agent, or Firm—Jenner & Block

[57] ABSTRACT

A system and method for cleaning, disinfecting, storing and wetting rigid gas permeable contact lenses is provided. The system includes a cleaning, disinfecting and storing solution and a separate wetting solution. Both solutions contain hydrophilic disinfectants or preservatives which do not inhibit proper wetting of rigid gas permeable contact lenses. The lenses are stored in the cleaning, disinfecting and storing solution during non-wearing periods. This storage also acts as a secondary or backup cleaning treatment to help remove any residual contaminants after the primary cleaning with this solution.

45 Claims, No Drawings

PRESERVATIVE SYSTEM FOR OPHTHALMIC AND CONTACT LENS SOLUTIONS AND METHOD FOR CLEANING DISINFECTING AND STORING CONTACT LENSES

RELATED APPLICATION

This application is a continuation-in-part of U.S. application Ser. No. 551,514, filed Jul. 11, 1990, now U.S. Pat. No. 5,141,665, which is a continuation of U.S. application Ser. No. 07/242,410, filed Sep. 9, 1988, which is a continuation-in-part of U.S. application Ser. No. 140,075, filed Dec. 31, 1987 which is a continuation-in-part of U.S. application Ser. No. 032,891, filed Mar. 31, 1987.

FIELD OF THE INVENTION

The present invention relates to a preservative system for contact lens solutions and to a rigid gas permeable contact lens cleaning, storing, conditioning and wetting system and method. More particularly, the present invention relates to a cleaning, storing, conditioning and wetting system and method for rigid gas permeable contact lenses that allows effective cleaning and conditioning and proper wetting of rigid gas permeable lenses. The present invention also relates to a preservative system that avoids ocular irritation that is suitable for use with ophthalmic solutions other than contact lenses, such as over-the-counter and prescription ophthalmic drug solutions.

BACKGROUND OF THE INVENTION

Rigid gas permeable (RGP) lenses are manufactured from materials that exhibit a high degree of polarity, resulting in a strong interaction with proteins and other tear constituents that ultimately produce tenacious surface deposits. Current state of the art care systems combat this problem through the use of unpreserved abrasive cleaners that produce microscopic scratches which, in time, shorten the useful life of the lens. Some attempts have been made to competitively block surface deposition by so-called "conditioning" solutions, but this approach involves the use of cytotoxic preservatives and does not eliminate the need for the abrasive cleaner.

Proteolytic enzymes have been of marginal value in controlling surface deposition because their action is limited to proteinaceous material. Multifunctional esterases capable of lysing both proteins and lipids failed to significantly improve on the results obtained with their proteolytic counterparts and the consequences of their usage was a delayed, but persistent, surface deposition and premature loss of the lens.

Aside from the problem of ultimate surface contamination, the RGP lens wearer is also faced with an initial discomfort problem until the lens completely hydrates, at which time it displays its best wetting and consequently its greatest comfort. In order to ensure that this maximal comfort is maintained, it is essential that the wettability of the surface be maintained. Moreover, the capability of the lens to resist surface deposition is also directly related to the maintenance of its wettability. The current state of the art lens care systems do not maintain optimal wettability over long periods of time because they are passive systems formulated to deal with the result of the polymer's surface interactions rather than to eliminate its cause.

RGP lenses have the potential of providing an unsurpassed level of comfort for a rigid lens. Unfortunately, the wearer realizes this benefit for only a short period of time because the current passive RGP care systems are unable to maintain this property.

Initial treatment of new RGP lenses usually includes cleaning with an abrasive cleaner, after which the lens may be soaked in a viscous, polar solution, to purportedly interact with active sites on the lens surface and thereby block their interaction with contaminants. The failure of this system to achieve this result is evident in the fact that the abrasive cleaner must be used on a daily basis and even then, adjunctive products are frequently needed. "Conditioning" then must require abrading the surface as part of the process. Aside from the lack of efficacy of this system, it shortens the functional life of the lens thereby producing a financial loss for the wearer.

The sequence of a separate cleaner (generally abrasive), a separate rinse solution, a separate soak solution, re-rinsing again after soaking and a separate wetting solution and a separate "in-eye" re-wetting solution or a system of a separate abrasive cleaner and a combined soaking, conditioning solution and a separate "in-eye" re-wetting solution is the basis for all known contact lens systems of hygiene other than the present invention. There are several serious objections to this sequence of operations.

Cleansing is a manual procedure that requires rubbing the lens between the fingers or in the palm of the hand. Only a small volume of cleaner is used and the procedure ideally (but rarely) requires at least 1 minute. Regardless of the chemical composition of the cleaning solution, this is primarily a physical procedure that involves the interaction of friction induced by the rubbing and the surfactant properties of the solution. In some cases, the friction is enhanced by the suspension of abrasive particles in the cleaner.

Abrasives added to improve on the cleansing action of manual procedures may damage the lens either by producing microscopic scratches and/or changing the lens parameters. Incomplete rinsing of cleaners that contain suspended abrasives may result in harmful residues that induce corneal damage.

Physical cleansing is also ineffective against bacteria that form biofilms. The common species of bacteria that have been linked to ocular infections, namely, pseudomonas aeruginosa and serratia marcescens, are known to secrete a slime-like covering of their cell walls to protect against a hostile environment. These organisms grow in contact lens cases despite the presence of a preserved soaking solution and may even contaminate bottles containing the solutions.

The use of a second solution for soaking and disinfecting usually results in the utilization of preservatives that are limited in their biocidal activity as a result of the requirement that they be non-irritating to ocular tissues. This situation came about because the manufacturers wanted to limit the number of steps required for lens care, hoping to encourage compliance. It was common practice for patients to remove their lenses from the soaking solution and place them directly on their eye therefore necessitating that they not irritate the ocular tissues. When rinsing was prescribed, the wearers were encouraged to use a rewetting drop so as to "cushion" the eye from the initial impact of a solution that might tend to irritate it.

In order to achieve some measure of effective hygiene, the manual system usually evolved into the use of 3 or 4 separate products, a cleaner, a viscous soaking/disinfecting solution, an enzymatic cleaner and sometimes a rewetting or cushioning drop. This resulted in a complicated, time-consuming regimen that discouraged compliance and added to the cost of lens care.

Known and/or FDA approved cleaning and wetting solutions for RGP contact lenses utilize hydrophobic preservatives or disinfecting agents such as benzalkonium chloride, chlorhexidine or polyamino-propyl biguanide. These hydrophobic materials tend to reduce the wettability of RGP lenses, especially fluorinated RGP lenses, thereby making cleaning and wetting more difficult. A surfactant polymer may be added to such formulations specifically to attempt to overcome the effect of the hydrophobic preservative.

A need exists for an active RGP lens care system that deals with the causes of surface deposition and poor wetting without resorting to the use of abrasives, cytotoxic chemicals or enzymes, and without the use of preservatives that reduce the wettability of the lenses.

A need also exists for a new preservative system for contact lens solutions and over-the-counter and prescription drug ophthalmic solutions.

SUMMARY OF THE INVENTION

In accordance with the present invention, a preservative system and a solution system and method for cleaning, conditioning and wetting rigid gas permeable (RGP) contact lenses and other contact lenses is provided. In addition, the preservative system is useful for maintaining the sterility of over-the-counter and prescription drug ophthalmic solutions.

Rigid gas permeable or RGP contact lenses feel rigid, similar to hard contact lenses, but have substantial gas permeability. RGP contact lenses are made or can be made from a number of materials. RGP lenses can be made from silicone acrylate (which may be fluorinated), silicone, styrene, fluorinated materials, urethane and similar materials. The fluorinated silicone acrylate material usually has greater oxygen permeability, which is beneficial to the wearer, but is more difficult to clean and wet. The system and method of the present invention is particularly suited for care of fluorinated silicone acrylate RGP contact lenses.

Preservatives or disinfectants used in prior RGP cleaning and wetting solutions, such as benzalkonium chloride and chlorhexidine, are electropositive, hydrophobic compounds. These compounds exhibit an affinity for the surface of RGP contact lenses, the material of which is electronegative. As a result, benzalkonium chloride or chlorhexidine becomes bound to the RGP lens surface. As a result, these preservatives, which are also hydrophobic, reduce the wettability of the RGP lens. In contrast, the preservatives or disinfectants in accordance with the present invention are electronegative and hydrophilic and do not deleteriously bind to the RGP lens.

The cleaning, conditioning and wetting solution system of the present invention includes a sterile aqueous cleaning, storing and conditioning solution and a separate, sterile aqueous wetting solution that is compatible with the cleaning and conditioning solution. The wetting solution can also be used as an in-eye lubricant. Preferably, the system should be obtained and used in kit form to ensure proper care of a person's RGP contact lenses. Both solutions, which are formulated for and are compatible with RGP lenses, avoid the use of a hydrophobic preservative or disinfectant, such as benzalkonium chloride, chlorhexidine or polyamino-propyl biguanide, which have been found to reduce the wettability of an RGP contact lens. This is especially the case with fluorinated RGP contact lenses. The need for an additional surfactant to attempt to overcome the hydrophobic properties of the preservative or disinfectant is eliminated. In accordance with the present invention, several additional advantages are provided. First, the need for a daily abrasive cleaner is avoided. Second, the need for ancillary products, such as enzyme cleaners, is eliminated, which is not the case with current state of the art systems not in accordance with the invention.

In one embodiment, the cleaning and conditioning components of the cleaning, conditioning and storing solution are specifically chosen to clean and condition RGP lenses, as well as be suitable for storage of RGP lenses. Storage of the contact lenses in the cleaning, conditioning and storage solution of the present invention provides a number of significant advantages over prior art contact lens solutions and treatment methods. This solution allows RGP lenses to be conditioned without abrading or damaging the surface of the lens and allows the lens to maintain its wettability and deposit resistance throughout the wearing period and without the need for adjunctive solutions, such as enzyme cleaners and in-eye lubricants, for example. Additional advantages include (1) removal of bacterial biofilms (including pseudomonas aeruginosa and serratia marcescens biofilm; (2) reduced eye irritation because of a cleaner lens surface; (3) use of only two solutions, one for cleaning, storing and disinfecting and one for wetting; and (4) it is effective for all types of RGP lenses.

The cleaning, conditioning and storage solution is a nonabrasive sterile aqueous solution that includes a hydrophilic disinfectant compound or compounds and a suitable component for cleaning and conditioning RGP contact lenses.

By hydrophilic disinfectant is meant that the disinfectant or preservative or combination of disinfectants or preservatives are hydrophilic. Preferably, none of the disinfectant compounds present in the solution are hydrophobic.

The disinfectant or preservative for the cleaning, conditioning and storing solution and for the wetting solution in accordance with the invention comprises two compounds, benzyl alcohol and a water soluble salt of ethylenediaminetetraacetic acid (EDTA or edetate), which is an adjuvant disinfectant, preferably the disodium or trisodium salt of EDTA. No other disinfectants are necessary. The disinfectant compounds are present in amounts effective to maintain the sterility of the composition. Usually, these amounts are about 0.05% to about 1.0% (preferably about 0.1%–0.3%) benzyl alcohol, and, for the cleaning solution, about 0.025% to about 0.75% (preferably about 0.5%) of the salt of EDTA (from about 0.025% to about 0.25 and preferably about 0.1 for the wetting solution), by weight of the total solution (whether a cleaning, wetting, conditioning or other solution), including water, will be effective for preserving the solution. In addition, the foregoing amount of benzyl alcohol (about 0.05 to 1.0%) and salt of EDTA (about 0.025 to 0.75%) provides the additional advantage of disinfecting contact lenses when the lenses are stored in such a solution during nonwearing periods. Alternatively, the cleaning solution and wetting solution disinfectant may comprise sorbic acid (usually about 0.001 to about 0.35% and preferably 0.1), a water soluble salt of EDTA (in an amount as previously described) and optionally boric acid (usually up to about 1.0% and preferably 0.6%). Boric acid is incompatible with polyvinyl alcohol (PVA) and thus should not be used in a wetting solution that contains PVA.

The benzyl alcohol used in accordance with the present invention should be a high purity benzyl alcohol, whether for a contact lens solution or ophthalmic drug solutions. It has been discovered that standard grades of benzyl alcohol available for pharmaceutical use contain significant amounts of benzaldehyde. Benzaldehyde is an impurity present in commercially available benzyl alcohol. While benzaldehyde does not appear to compromise the bactericidal activity of benzyl alcohol, it has been discovered that benzaldehyde, when present in contact lens solutions in sufficient concentration, acts as an eye irritant. Benzyl alcohol at high enough concentrations (about 2% by weight or more) can also act as an ocular irritant and such benzyl alcohol concentrations should be avoided.

The benzyl alcohol that is incorporated in the contact lens solutions and ophthalmic drug solutions of the present invention should be free of a benzaldehyde concentration such that when incorporated into a contact lens solution, an excessive benzaldehyde concentration would result, and is sometimes referred to herein as "high purity benzyl alcohol." As used herein "excessive benzaldehyde concentration" means that concentration of benzaldehyde which causes significant eye irritation. Usually, in accordance with the invention, the concentration of benzaldehyde in the final contact lens solution should be no more than about one ppm (by weight of the total solution) and preferably under about one ppm by weight of the total solution, and most preferably about 0.1 ppm or less by weight of the total solution.

Suitable benzyl alcohol (high purity benzyl alcohol) for use in accordance with the invention can be obtained from Akzo Chemic America of Edison, N.J. and Stauffer Chemical Company of Westport, Conn., a subsidiary of Chesebrough Ponds Inc. Akzo Chemic can provide, for example, benzyl alcohol containing less than about 100 ppm benzaldehyde by weight benzyl alcohol. Methods of removing benzaldehyde from benzyl alcohol are well known to those skilled in the art. Typically, "high purity benzyl alcohol," as used in accordance with the invention will be benzyl alcohol suitable for pharmaceutical use and having a benzaldehyde concentration of less than or equal to about 100 ppm by weight of the benzyl alcohol.

An antioxidant material can be present in the composition to prevent or minimize oxidation of the benzyl alcohol. Suitable antioxidants that can be used include sodium bisulfite and various forms of Vitamin A, such as esters of Vitamin A, preferably Vitamin A palmitate, which has a biopotency of about $1.7 \times 10^6$ I.U./gram.

In accordance with another aspect of the invention, the disinfectant consists of, or consists essentially of, two compounds. This two component combination can be benzyl alcohol and a water soluble salt of EDTA, or sorbic acid and a water soluble salt of EDTA in amounts as previously specified. Thus, disinfectant materials such as chlorhexidine, benzalkonium chloride, thimerosal, trimethoprim, polyamino-propyl biguanide, or some other disinfectant, are not needed or used in accordance with the invention. Moreover, materials such as trimethoprim have low solubility in water and thus are hydrophobic. Such materials normally would not be contemplated for use in accordance with the invention.

The cleaning and conditioning component may comprise an alkylarylpolyether alcohol non-ionic detergent and an amphoteric surface active agent in effective amounts for cleaning and conditioning an RGP contact lens. This combination of materials has been found effective to clean and condition RGP contact lenses. By "condition" is meant that the RGP lens surface is cleaned and that surface interactions which inhibit wetting (such as a surface charge) are eliminated or neutralized. The cleaning and conditioning component is compatible with RGP lenses so as to allow storage of the lenses in the cleaning, conditioning and storage solution. Usually, about 0.5% to about 10% of the amphoteric surface active agent and from about 0.005% to about 5.0% of the alkylarylpolyether alcohol, by weight of the total cleaning, conditioning and storing solution, including water, will be effective for providing the desired cleaning and conditioning of RGP lenses, and will permit storage of the lenses in the solution. Other types of cleaning components may be suitable for use in accordance with the invention, as long as the desired cleaning and conditioning of RGP contact lenses is provided.

In accordance with another aspect of the invention, the cleaning, storing and conditioning solution consists of, or consists essentially of: (a) a hydrophilic preservative consisting of (i) benzyl alcohol and a water soluble salt of EDTA or (ii) sorbic acid and a water soluble salt of EDTA; (b) at least one cleaning and conditioning component; and (c) sterile water. Various additional components may also be included as specified in the following Description of The Preferred Embodiments and as recited in Tables 1 and 2.

The wetting solution of the present invention is a sterile aqueous solution that includes a hydrophilic preservative or disinfectant and at least one wetting agent selected from polyvinyl alcohol (PVA) and polyvinylpyrrolidone (PVP). PVA is preferred over PVP.

The hydrophilic preservative can be as previously described and may also include sorbic acid as an adjuvant bactericide, usually in the range of from about 0.001% to about 0.20% by weight of the total composition.

In accordance with another aspect of the invention the wetting solution may consist of or consist essentially of: (a) a hydrophilic preservative consisting of, or consisting essentially of, (i) benzyl alcohol and a water soluble salt of EDTA; or (ii) sorbic acid and a water soluble salt of EDTA; (b) at least one wetting agent selected from PVA and PVP; and (c) sterile water. Various additional components may also be present as recited in the following Description of The Preferred Embodiments and as recited in Tables 3 and 5.

Preferably, the wetting solution has a tonicity of from about 0.91 to about 1.65 and a pH in the range of from about 6.5 to 8.5. Various salts and buffers can be included to provide the desired tonicity and pH.

In accordance with a broader aspect of the invention, a new preservative system is provided that can be used for numerous types of contact lens solutions, including solutions for hard, soft and gas permeable contact lenses as well as other ophthalmic solutions, such as over-the-counter and prescription ophthalmic drug solutions. Examples of such drugs include dexamethasone phosphate, pilocarpine hydrochloride, and phenylephrine hydrochloride, for example. The preservative system comprises high purity benzyl alcohol in an amount sufficient to preserve the sterility of the solution. Usually, the benzyl alcohol will be present in an amount of from about 0.05% to about 1.0% by weight of the total composition. The high purity benzyl alcohol used in accordance with the invention can be used as a preservative for a wide variety of contact lens solutions, including, for example, wetting, rinsing, soaking and cleaning solutions, in-eye wetting and rewetting solutions, and sterilizing and storage solutions, which can be saline solutions.

In accordance with another aspect of the present invention, a cold disinfecting aqueous solution for disinfecting soft contact lenses is provided that comprises high purity benzyl alcohol and isopropyl alcohol in effective amounts for disinfecting soft contact lenses. Generally, the effective amounts of high purity benzyl alcohol in this solution is in the range of from about 0.05 to about 1.0% (preferably 0.33%) and isopropyl alcohol in the range of from about 0.1% to about 5.0% (preferably about 1.5%) all by weight of the total composition. Preferably, a water soluble salt of EDTA is present in an amount in the range of from about 0.025% to about 0.75% (preferably about 0.15%) by weight of the total composition.

A preferred soft contact lens disinfecting cold (ambient) temperature storing solution utilizes a polyoxyalkylated nonionic detergent and has the formula (% by weight): Tween 80 (polyoxylated detergent) 0.6%, Tween 20 0.6%, boric acid 1.15%, sodium borate 0.4%, disodium EDTA 0.15%, isopropyl alcohol 1.5%, and high purity benzyl alcohol (less than 100 ppm benzaldehyde) 0.33%.

The foregoing solution removes microorganism biofilm from soft contact lenses as part of the disinfecting process by storage of the soft lenses therein. While not wishing to be bound by theory, it is believed that the presence of benzyl alcohol, isopropyl alcohol, salt of EDTA and nonionic detergent results in a cold disinfecting solution that is compatible with soft contact lenses and removes biofilm. Also, it is believed that the presence of one or more detergents in the disinfecting and cleaning, storing and conditioning solutions of the present invention enhances the effectiveness of the benzyl alcohol and salt of EDTA.

Contact lens solutions in accordance with the present invention have been approved by the United States Food and Drug Administration.

DESCRIPTION OF THE PREFERRED EMBODIMENTS

RGP lenses destined for the solution system and method of the present invention should preferably be cleaned with the cleaning, conditioning and storing solution as follows. The lens is placed in the palm of the hand and then covered with the solution. The lens is then bathed and patted with the index finger of the other hand. The lens should not be rubbed, for example, such as between the thumb and forefinger, since this may warp or scratch the lens.

After cleaning, between wearing periods, the lenses should be thoroughly rinsed with tap water and then stored in the cleaning, conditioning and storing solution. Usually, regardless of the wearer's cleaning technique and type of cleaning solution, some residual contaminants will remain on the lens. Because the cleaning solution of the present invention is also the storage solution, and because of its formulation, at least a portion of, if not all, residual contaminants are removed or loosened during storage. This is contrary to the prior art, which does not contemplate utilizing a cleaning solution for storage. Such a system is especially advantageous since the wearer may often fail to clean the lens properly or sufficient, or may even forget to clean the lens at all, prior to storage. Thus, storage of the lens in the cleaning, storing and conditioning solution acts as a secondary or backup cleaning treatment, in addition to storing and otherwise conditioning the lens. When one desires to wear the lenses, they should be rinsed with tap water or fresh saline, wetted with the wetting solution of the present invention and inserted into the wearer's eye.

An especially preferred cleaning, conditioning and storage solution in accordance with the invention and especially suitable for RGP contact lenses has the composition:

TABLE 1

| Component | Amount (% by weight) |
| --- | --- |
| Amphoteric surface active agent (Miranol 2 MCA Modified) | 8.0 |
| alkylarylpolyether alcohol (Triton X-100) | 2.33 |
| high purity benzyl alcohol (less than 100 ppm benzaldehyde) | 0.3 |
| trisodium or disodium edetate | 0.5 |
| propylene glycol | 2.0 |
| purified water | to 100 |

One preferred type of amphoteric surface active agent is 2-cocoyl-2-imidazolinium lauryl sulfate-1-carboxymethyloxyethyl-1-carboxymethyl disodium which is also sold under the trade name "Miranol 2 MCA Modified" by the Miranol Chemical Company, Inc. of Irvington, N.J. The amphoteric surface active agent is present in the preferred composition of the present invention in an amount of from about 0.5% to about 20% of the total weight of the aqueous composition and preferably comprises about 8.0% of the total aqueous composition. One substitute for "Miranol 2 MCA Modified" is "Miranol MHT" which is also sold by the Miranol Chemical Company, Inc.

The preferred type of alkylarylpolyether alcohol in the cleaning, conditioning and storing composition of the present invention is isooctylphenoxypolyethoxyethanol. The most preferred type of isooctylphenoxypolyethoxyethanol contains about 9 units of ethoxyethanol per unit of isooctylphenol and has a molecular weight of about 630. The most preferred alkylarylpolyether alcohol is sold under the trademark "Triton X-100" by the Rohm & Haas Company of Philadelphia, Pa. The alkylarylpolyether alcohol is present in a concentration of from about 0.005% to about 5.0%, and preferably about 2.33%, by weight of the total aqueous composition. The alkylarylpolyether alcohols are also known as octylphenolethyleneoxide. The alkylarylpolyether alcohol complements the cleansing characteristics of the block copolymers and helps to remove ocular secretions, proteinaceous deposits and other materials which may be deposited upon the surfaces of the lens.

Preferably, propylene glycol is present in the cleaning compositions in accordance with the invention in an amount of from about 0.005% to about 5.0% by weight of the total aqueous composition. Propylene glycol helps provide for ease of rinsing the cleaning composition from the contact lens surface and also acts as a preservative of the composition and a thickening agent.

The cleaning, conditioning and storing solution in accordance with the invention generally has a pH of from about 5.0 to about 6.5. This slightly acidic pH helps to dissolve protein and aids in rinsing the composition from the lens.

Another example of a cleaning, conditioning and storing composition in accordance with the invention which is suitable for RGP contact lenses is:

TABLE 2

| Component | Amount (% by weight) |
|---|---|
| Miranol 2 MCA Modified | 8.0 |
| propylene glycol | 0.67 |
| Triton X-100 | 2.33 |
| trisodium edetate | 0.5 |
| sorbic acid | 0.1 |
| sodium bisulfite (optional) | 0.05 |
| sterile water | to 100 |

Preferably, sodium bisulfite is not included in the foregoing composition.

An especially preferred wetting solution in accordance with the present invention which is especially suitable for RGP lenses has the composition:

TABLE 3

| Component | Amount (% by weight) |
|---|---|
| polyvinyl alcohol | 1.0 |
| polyvinylpyrrolidone (Plasdone ® C) (optional) | 0.5 |
| high purity benzyl alcohol (less than 100 ppm benzaldehyde) | 0.1 |
| disodium or trisodium edetate | 0.1 |
| sorbic acid | 0.05 |
| hydroxyethylcellulose | 0.35 |
| sodium bisulfite (optional) | 0.02 |
| sodium carbonate | 0.1375 |
| sodium phosphate | 0.005 |
| sodium biphosphate | 0.005 |
| sodium chloride | 0.748 |
| potassium chloride | 0.280 |
| sterile water | to 100 |

It is preferred not to include sodium bisulfite in the foregoing composition. The high purity benzyl alcohol listed in Table 3 is obtained from Akzo Chemic and has a benzaldehyde concentration of 82 ppm. Another preferred wetting solution in accordance with the invention for RGP contact lenses has the composition:

TABLE 4

| Component | Amount (% by weight) |
|---|---|
| polyvinyl alcohol | 1.0 |
| high purity benzyl alcohol (less than 100 ppm benzaldehyde) | 0.15 |
| disodium edetate | 0.1 |
| hydroxyethylcellulose | .20 |
| sodium carbonate | 0.1375 |
| sodium phosphate | 0.005 |
| sodium biphosphate | 0.005 |
| sodium chloride | 0.748 |
| potassium chloride | 0.280 |
| sterile water | to 100 |

Another cleaning composition in accordance with the invention, which is especially useful for cleaning soft contact lenses has the formula:

TABLE 5

| Component | Amount (% by weight) |
|---|---|
| Miranol 2 MCA | 3.0 |
| Pluronic F108 | 6.0 |
| Triton X-100 | 0.5 |
| propylene glycol | 1.0 |
| high purity benzyl alcohol (less than 100 ppm benzaldehyde) | 0.1 |
| disodium or trisodium edetate | 0.5 |
| potassium chloride | 0.3 |
| sodium chloride | 0.616 |
| sodium bicarbonate | 0.05 |
| USP purified water | to 100 |

Another cleaning composition in accordance with the invention especially useful for cleaning soft contact lenses has the formula:

TABLE 6

| Component | Amount (% by weight) |
|---|---|
| Miranol 2 MCA | 3.0 |
| Pluronic F108 | 6.0 |
| Triton X-100 | 0.5 |
| propylene glycol | 1.0 |
| high purity benzyl alcohol (less than 100 ppm benzaldehyde) | 0.3 |
| disodium edetate | 0.5 |
| potassium chloride | 0.3 |
| sodium chloride | 0.616 |
| sodium bicarbonate | 0.05 |
| USP purified water | to 100 |

An especially suitable wetting and in-eye comfort drop for soft and RGP contact lenses and lens wearers has the formula:

TABLE 7

| Component | Amount (% by weight) |
|---|---|
| high purity benzyl alcohol (less than 100 ppm benzaldehyde) | 0.1 |
| Polysorbate 80 (Vitamin A emulsifier) | 0.1 |
| Vitamin A Palmitate ($1.7 \times 10^6$ I.V./gram) | 0.0196 |
| polyvinylpyrrolidone | 0.5 |
| polyvinyl alcohol | 1.0 |
| hydroxyethylcellulose | 0.27 |
| disodium or trisodium EDTA | 0.1 |
| potassium chloride | 0.28 |
| sodium chloride | 0.6 |
| sodium biphosphate | 0.005 |
| sodium phosphate | 0.005 |
| sodium carbonate | 0.02 |
| USP purified water | to 100 |

A preferred wetting and in-eye comfort drop for soft and RGP contact lenses and lens wearers has the formula:

TABLE 8

| Component | Amount (% by weight) |
|---|---|
| high purity benzyl alcohol (less than 100 ppm benzaldehyde) | 0.15 |
| polyvinyl alcohol | 1.0 |
| hydroxyethylcellulose | 0.2 |
| disodium EDTA | 0.1 |
| potassium chloride | 0.28 |
| sodium chloride | 0.6 |
| sodium biphosphate | 0.005 |
| sodium phosphate | 0.005 |
| sodium carbonate | 0.02 |
| USP purified water | to 100 |

An especially suitable wetting and in-eye comfort drop for RGP lenses (such as silicone acrylate and fluorosilicone acrylate RGP lenses) and lens wearers has the formula:

TABLE 9

| Component | Amount (% by weight) |
| --- | --- |
| high purity benzyl alcohol (less than 100 ppm benzaldehyde) | 0.1 |
| sorbic acid | 0.05 |
| sodium bisulfite (optional) | 0.02 |
| polyvinylpyrrolidone | 0.5 |
| polyvinyl alcohol | 1.0 |
| hydroxyethylcellulose | 0.33 |
| disodium or trisodium edetate | 0.1 |
| potassium chloride | 0.280 |
| sodium chloride | 0.6 |
| sodium biphosphate | 0.005 |
| sodium phosphate | 0.005 |
| sodium carbonate | 0.06 |
| USP purified water | to 100 |

Another preferred wetting and in-eye comfort drop for RGP lenses (such as silicone acrylate and fluorosilicone acrylate RGP lenses) and lens wearers has the formula:

TABLE 10

| Component | Amount (% by weight) |
| --- | --- |
| high purity benzyl alcohol (less than 100 ppm benzaldehyde) | 0.15 |
| polyvinyl alcohol | 1.0 |
| hydroxyethylcellulose | 0.2 |
| disodium edetate | 0.1 |
| potassium chloride | 0.280 |
| sodium chloride | 0.6 |
| sodium biphosphate | 0.005 |
| sodium phosphate | 0.005 |
| sodium carbonate | 0.06 |
| USP purified water | to 100 |

The wetting solution includes at least one component suitable for wetting contact lenses. The wetting system can include a viscosity-building agent and a wetting agent suitable for RGP contact lenses. Suitable viscosity-building agents include water soluble cellulosic polymers, which may be synthetic or natural, for example. Such materials also assist in wetting the lenses. Suitable wetting agents include polyvinyl alcohol and polyvinylpyrrolidone and mixtures thereof, for example. Other suitable viscosity-building agents and wetting agents for RGP contact lens wetting solutions can be used.

Suitable cellulosic polymers include hydroxyethylcellulose, methylcellulose, carboxymethylcellulose, natural gums and mixtures thereof. Usually, the amount of cellulosic polymer present in the composition is from about 0.05% to about 0.80% by weight of the total composition.

Usually, the wetting composition will have a viscosity of between about 2 to 40 cps at 25° C. and preferably a viscosity of between about 2 and 20 cps at 25° C. Medium grade cellulosic polymers are useful for achieving the desired viscosity.

In the especially preferred composition of Table 3, sorbic acid functions as a preservative and, when present, will usually be in the range of from about 0.001% to about 0.35%, preferably about 0.05%.

Preferably, the polyvinyl alcohol utilized is partially hydrolized. Generally, the amount of polyvinyl alcohol present in the composition is from about 0.5% to about 2.5% by weight of the total composition.

An additional wetting compound, a polyvinylpyrrolidone polymer, can be utilized, usually in an amount of from about 0.5% to about 2.0% by weight of the total composition. A preferred polyvinylpyrrolidone is available from GAF Corporation of New York, N.Y. under the name Plasdone ® C.

It is to be understood that the invention is not limited to the foregoing types of wetting agents and viscosity-building agents. Any type of material which can be used to provide the desired wetting action for RGP contact lenses, or other contact lenses, and which is compatible with the preservative system of the present invention and is otherwise suitable for use in a wetting solution or an RGP or other contact lens wetting solution can be utilized.

An especially preferred wetting system contains hydroxyethylcellulose and polyvinyl alcohol. A preferred hydroxyethylcellulose is available from Hercules, Inc. of Wilmington, Del. under the trade designation "250 H." A preferred polyvinyl alcohol is available from the Monsanto Company of St. Louis, Mo. under the name of "Galvatol" which is partially hydrolized.

The wetting compositions of the present invention are preferably buffered and slightly acid or neutral. The preferred pH range is from about 6.5 to about 8.5. Suitable buffers are known in the art. Especially suitable buffers include sodium bicarbonate and tribasic sodium phosphate ($Na_3PO_4.12H_2O$). The preferred combination of buffers is sodium bicarbonate, tribasic sodium phosphate and sodium biphosphate ($NaH_2PO_4).H_2O$, in amounts to provide and maintain the desired pH.

The remainder of the wetting composition is sterile water U.S.P. and preferably includes combinations of essentially neutral and alkaline salts compatible with ocular tissue and RGP contact lens materials, generally present in a concentration to provide an aqueous composition salt content equivalent to from about 0.91 to about 1.65 tonicity. Sodium chloride can be present in the RGP contact lens wetting composition in an amount from about 0.05% to about 2.0% by weight of the total aqueous composition, for example, and preferably in an amount of about 0.75% by weight of the total aqueous composition. Potassium chloride is another salt which is preferably used in conjunction with sodium chloride and should generally be present in an amount of from about 0.05% to about 2.0% by weight of the total aqueous composition and preferably in an amount of about 0.28% by weight of the total aqueous composition.

Another wetting composition for RGP contact lenses in accordance with the invention is:

TABLE 11

| Component | Amount (% by weight) |
| --- | --- |
| polyvinylpyrrolidone (Plasdone ® C) | 2.0 |
| sorbic acid | 0.1 |
| boric acid | 0.6 |
| trisodium EDTA | 0.1 |
| hydroxyethylcellulose | 0.32 |
| sodium bisulfite (optional) | 0.02 |
| sodium carbonate | 0.14 |
| sodium phosphate | 0.005 |
| sodium biphosphate | 0.005 |
| sodium chloride | 0.75 |
| potassium chloride | 0.28 |
| sterile water | to 100 |

Preferably, sodium bisulfite is absent from the foregoing compositions.

A daily cold disinfecting solution for soft contact lenses in accordance with the invention has the formula:

TABLE 12

| Component | Amount (% by weight) |
| --- | --- |
| high purity benzyl alcohol (less than 100 ppm benzaldehyde) | 0.3 |
| monaquat P-TC detergent | 0.001–1.0 (preferably 0.005) |
| boric acid | 1.15 |
| sodium borate | 0.4 |
| trisodium edetate | 0.15 |
| Tween 20 | 0.06 |
| Tween 80 | 0.06 |
| isopropyl alcohol | 0.05 |
| USP purified water | to 100 |

The cold disinfecting solution can be used, for example, the cleaning and then storing the soft lenses in the solution during nonwearing periods, such as overnight.

A preferred daily cold cleaning, disinfecting, storage and rinsing solution for soft (HEMA) contact lenses has the formula:

TABLE 13

| Component | Amount (% by weight) |
| --- | --- |
| boric acid | 1.15 |
| sodium borate | 0.4 |
| disodium EDTA or trisodium edetate | 0.15 |
| monaquat P-TC | 0.0085 |
| Tween 20 | 0.12 |
| high purity benzyl alcohol (less than 100 ppm benzaldehyde) | 0.3 |
| USP purified water | to 100 |

Another preferred cold cleaning, disinfecting, storage and rinsing solution for soft contact lenses in accordance with the invention has the formula:

TABLE 14

| Component | Amount (% by weight) |
| --- | --- |
| Tween 80 | 0.12 |
| boric acid | 1.15 |
| sodium borate | 0.4 |
| disodium EDTA or trisodium edetate | 0.15 |
| monaquat P-TC | 0.0075 |
| isopropyl alcohol | 2.5 |
| high purity benzyl alcohol (less than 100 ppm benzaldehyde) | 0.3 |
| USP purified water | to 100 |

Preferably, the disinfecting solutions for soft contact lenses include from about 0.05% to 5.0% isopropyl alcohol as an adjuvant preservative and disinfectant.

A preferred non-abrasive soft contact lens cleaner has the formula:

TABLE 15

| Component | Amount (% by weight) |
| --- | --- |
| sodium carbonate | 0.025 |
| sodium chloride | 0.616 |
| potassium chloride | 0.3 |
| trisodium edetate (EDTA) | 0.5 |
| high purity benzyl alcohol (less than 100 ppm benzaldehyde) | 0.3 |
| propylene glycol | 1.0 |
| Triton X-100 | 0.5 |
| Pluronic F108 | 6.0 |
| Miranol 2 MCA | 3.0 |
| USP purified water | to 100% |

EXAMPLE 1

A study was conducted to evaluate the preservative efficacy with rechallenge of contact lens solutions in accordance with the invention according to *United States Pharmacopeia* (USP) Twenty-First Revision and the Draft Testing Guidelines for Class III Contact Lens Solutions, July 1985 Revision.

The test system consisted of:
*Staphylococcus aureus*, ATCC 6538
*Pseudomonas aeruginosa*, ATCC 9027
*Candida albicans*, ATCC 10231
*Aspergillus niger*, ATCC 16404
*Escherichia coli*, ATCC 8739
from STS Rept. M 88-778.

The challenge organisms were prepared as follows.

*E. coli*, *P. aeruginosa* and *S. aureus* were inoculated onto Tryptic Soy Agar (TSA) slants and incubated for 18-24 hours at 32°-35° C., transferred onto fresh TSA slants and reincubated for 18-24 hours at 32°-35° C. The cultures were harvested with 0.067M phosphate buffer and washed using the following procedure:

a. Centrifuged at 5,000 rpm at 5° C. for 10 minutes.
b. Supernatant decanted.
c. The pellet resuspended with fresh phosphate buffer.
d. a-c was repeated once.

*C. albicans* was grown on Sabouraud Dextrose Agar (SDA) slants at 20°-25° C. for 24-48 hours and prepared in the same manner as the bacteria.

*A. niger* was grown on Tryptic Soy Agar Sabouraud Dextrose Agar (SDA) slants for 5-7 days at 20°-25° C. The spores were harvested using phosphate buffer with 0.1% Tween 80. The spores were washed in the same manner as the bacteria.

The concentration of all challenge organisms was adjusted spectrophotometrically with phosphate buffer to approximately $2 \times 10^8$ organisms/ml.

For each challenge organism, the following solutions were aseptically dispensed into sterile tubes: Test solution 20 ml of a contact lens solution having the formula set forth in Table 7 and a positive control 20 ml 0.1% peptone.

These tubes were inoculated with 0.1 ml of the appropriate inoculum suspension (approximately $1 \times 10^6$ organisms/ml) and mixed thoroughly. The final concentration was between $10^5$ and $10^6$ cfu/ml.

Within 15 minutes after the addition of the inoculum suspension and at 7, 14, 21 and 28 days exposure a 1.0 ml aliquot was aseptically removed from each tube and added to 9.0 ml sterile Dey Engley Broth (DEB) ($10^{-1}$ dilution). These samples were serially diluted in DEB to $10^{-3}$ (1 ml into 9 ml DEB twice sequentially). 0.1 ml and 1.0 ml aliquots from the $10^{-1}$ and $10^{-3}$ dilutions were plated using the pour plate method with Dey Engley Broth (DEB).

Due to growth in the positive control solution at later exposure times, dilutions were carried out to a final concentration of $10^{-7}$. Plates were incubated at 30°-35° C. for 48-72 hours. Following incubation, plate counts were recorded and challenge organism reduction was determined. Test and control solutions were stored at 20°-25° C. for the duration of the 28 day test.

The rechallenge evaluation was conducted as follows.

Fresh inoculum suspensions of the challenge organisms were prepared as in 1.0 and 2.0.

1:9 dilutions of 4.1 were prepared with phosphate buffer to an approximate concentration of $2.0 \times 10^7$ organisms/ml.

Immediately following the fourteen (14) day plating, all samples except the positive control were rechallenged with 0.1 ml of the appropriate challenge organism.

An additional positive control was prepared to verify the concentration and monitor the growth of the rechallenge inoculum for the remainder of the twenty-eight (28) day test period.

Within fifteen (15) minutes of the addition of the rechallenge and at twenty-one (21) and twenty-eight (28) days exposure, samples were taken, diluted and plated as in 3.3.

A neutralizer efficacy screen was completed for each exposure time and consisted of a one ml of uninoculated test solution being aseptically added to a 9.0 ml DEB blank and thoroughly mixed. Duplicate 1 ml aliquots from the Broth were transferred to petri plates and one ml of a *Bacillus subtilis* spore suspension (containing approximately 100 cells/ml) was added. All plates were poured using Dey Engley Agar. The plates were incubated at 32°-35° C. for 48-72 hours.

The results of this study are presented as follows.

Tables 16-20 each table showing the CFU (Colony forming units) of organism in the test solution and positive controls at each time point. Neutralizer Efficacy results found in Table 21.

The concentrations of *S. aureus*, *P aeruginosa* and *E. coli* were reduced to at least 0.1% (three log values) of the initial concentration within the first fourteen (14) days. The concentration of viable *C. albicans* and *A. niger* remained at or below the initial concentration during the first fourteen (14) days.

After rechallenge, the concentrations of *S. aureus*, *P. aeruginosa*, *C. albicans* and *A. niger* remained within the specifications for preservative efficacy with rechallenge.

*E. coli* was mistakenly rechallenged at a concentration of approximately $10^6$ which is one log higher than the specified level. This additional organic load resulted in a reduction of slightly less than 3 log values. It is believed a $10^5$ challenge would have resulted in a full 3 log reduction value. The belief that *E. coli* would have been reduced by 3 logs is further supported by the fact that in this test *P. aeruginosa* was reduced by at least 4 logs.

The concentration of the positive controls were not reduced more than 90.0% (one log value).

There was no significant reduction of *B. subtilis* during the Neutralizer Efficacy Screen.

The contact lens solution in accordance with the invention and as tested with *S. aureus*, *P. aeruginosa*, *C. albicans* and *A. niger* meet the requirements of Preservative Efficacy with rechallenge. *E. coli* was overchallenged by 90% of the 14 day rechallenge time; however, reduction of this organism was approximately 3 log values.

TABLE 16

*S. aureus*

| Time Interval | System Evaluated | Dilution | A Plate Count | B Plate Count | Average A&B CFU/ml |
|---|---|---|---|---|---|
| T = 0 day | Test | $10^4$ | 71 | 78 | $7.5 \times 10^5$ |
| | PC* | $10^5$ | 40 | 43 | $4.2 \times 10^6$ |
| T = 7 day | Test | $10^1$ | 0 | 0 | <10 |
| | PC | $10^6$ | 146 | 62 | $1.0 \times 10^8$ |
| T = 14 day | Test | $10^1$ | 0 | 0 | <10 |
| | PC | $10^6$ | 106 | 140 | $1.2 \times 10^8$ |
| T = 14 day Rechallenge | Test | $10^3$ | 255 | 265 | $2.6 \times 10^5$ |
| | PCR** | $10^3$ | 260 | 238 | $2.5 \times 10^5$ |
| T = 21 day | Test | $10^1$ | 0 | 0 | <10 |

TABLE 16-continued

*S. aureus*

| Time Interval | System Evaluated | Dilution | A Plate Count | B Plate Count | Average A&B CFU/ml |
|---|---|---|---|---|---|
| | PC | $10^7$ | 86 | 47 | $6.7 \times 10^8$ |
| | PCR | $10^6$ | 142 | 159 | $1.5 \times 10^8$ |
| T = 28 day | Test | $10^1$ | 0 | 0 | <10 |
| | PC | $10^6$ | 55 | 17 | $3.7 \times 10^7$ |
| | PCR | $10^6$ | 72 | 77 | $7.4 \times 10^7$ |

*Positive Control
**Rechallenge Positive Control

TABLE 17

*P. aeruginosa*

| Time Interval | System Evaluated | Dilution | A Plate Count | B Plate Count | Average A&B CFU/ml |
|---|---|---|---|---|---|
| T = 0 day | Test | $10^4$ | 43 | 84 | $6.4 \times 10^5$ |
| | PC* | $10^5$ | 116 | 178 | $1.5 \times 10^6$ |
| T = 7 day | Test | $10^1$ | 0 | 0 | <10 |
| | PC | $10^5$ | approx 1000 | approx 1000 | $1.2 \times 10^8$ |
| T = 14 day | Test | $10^1$ | 0 | 0 | <10 |
| | PC | $10^7$ | 50 | 30 | $4.0 \times 10^8$ |
| T = 14 day Rechallenge | Test | $10^3$ | 284 | 219 | $2.5 \times 10^5$ |
| | PCR | $10^3$ | 138 | 163 | $1.5 \times 10^5$ |
| T = 21 day | Test | $10^1$ | 50 | 47 | $4.9 \times 10^2$ |
| | PC | $10^7$ | 168 | 155 | $1.6 \times 10^9$ |
| | PCR | $10^7$ | 63 | 65 | $6.4 \times 10^8$ |
| T = 28 day | Test | $10^1$ | 0 | 0 | <10 |
| | PC | $10^7$ | 74 | 65 | $7.0 \times 10^8$ |
| | PCR | $10^7$ | 32 | 35 | $3.4 \times 10^8$ |

TABLE 18

*E. coli*

| Time Interval | System Evaluated | Dilution | A Plate Count | B Plate Count | Average A&B CFU/ml |
|---|---|---|---|---|---|
| T = 0 day | Test | $10^4$ | 95 | 126 | $1.1 \times 10^6$ |
| | PC | $10^4$ | 182 | 176 | $1.8 \times 10^6$ |
| T = 7 day | Test | $10^3$ | 51 | 67 | $5.9 \times 10^4$ |
| | PC | $10^7$ | 42 | 31 | $3.6 \times 10^8$ |
| T = 14 day | Test | $10^1$ | 1 | 1 | $1.0 \times 10^1$ |
| | PC | $10^7$ | 37 | 46 | $4.2 \times 10^8$ |
| T = 14 day Rechallenge | Test | $10^4$ | 52 | 44 | $4.8 \times 10^5$ |
| | PCR | $10^5$ | 7 | 15 | $1.1 \times 10^6$ |
| T = 21 day | Test | $10^3$ | 115 | 162 | $1.4 \times 10^5$ |
| | PC | $10^6$ | 164 | 150 | $1.6 \times 10^8$ |
| | PCR | $10^6$ | 77 | 63 | $7.0 \times 10^7$ |
| T = 28 day | Test | $10^2$ | 52 | 21 | $3.7 \times 10^3$ |
| | PC | $10^7$ | 61 | 55 | $5.8 \times 10^8$ |
| | PCR | $10^6$ | 315 | 301 | $3.1 \times 10^8$ |

TABLE 19

*C. albicans*

| Time Interval | System Evaluated | Dilution | A Plate Count | B Plate Count | Average A&B CFU/ml |
|---|---|---|---|---|---|
| T = 0 day | Test | $10^4$ | 72 | 70 | $7.1 \times 10^5$ |
| | PC | $10^4$ | 119 | 100 | $1.1 \times 10^6$ |
| T = 7 day | Test | $10^4$ | 142 | 150 | $1.5 \times 10^6$ |
| | PC | $10^7$ | 66 | 77 | $7.2 \times 10^8$ |
| T = 14 day | Test | $10^3$ | 102 | 108 | $1.1 \times 10^5$ |
| | PC | $10^6$ | 98 | 96 | $9.7 \times 10^7$ |
| T = 14 day Rechallenge | Test | $10^4$ | 24 | 37 | $3.1 \times 10^5$ |
| | PCR | $10^3$ | 102 | 109 | $1.1 \times 10^5$ |
| T = 21 day | Test | | | | |
| | PC | $10^5$ | 90 | 87 | $8.9 \times 10^6$ |
| | PCR | $10^7$ | 55 | 65 | $6 \times 10^8$ |
| T = 28 day | Test | $10^3$ | 62 | 96 | $7.9 \times 10^4$ |

TABLE 19-continued

| | | | C. albicans | | |
|---|---|---|---|---|---|
| Time Interval | System Evaluated | Dilution | A Plate Count | B Plate Count | Average A&B CFU/ml |
| | PC | $10^5$ | 110 | 83 | $9.7 \times 10^6$ |
| | PCR | $10^6$ | 270 | 212 | $2.4 \times 10^8$ |

TABLE 20

| | | | A. niger | | |
|---|---|---|---|---|---|
| Time Interval | System Evaluated | Dilution | A Plate Count | B Plate Count | Average A&B CFU/ml |
| T = 0 day | Test | $10^5$ | 28 | 23 | $2.6 \times 10^6$ |
| | PC | $10^5$ | 20 | 25 | $2.3 \times 10^6$ |
| T = 7 day | Test | $10^3$ | 143 | 91 | $1.2 \times 10^5$ |
| | PC | $10^7$ | 52 | 37 | $4.5 \times 10^8$ |
| T = 14 day | Test | $10^2$ | 47 | 52 | $5 \times 10^3$ |
| | PC | $10^7$ | 31 | 30 | $3.1 \times 10^8$ |
| T = 14 day Re-challenge | Test | $10^3$ | 161 | 149 | $1.5 \times 10^5$ |
| | PCR | $10^4$ | 10 | 12 | $1.1 \times 10^5$ |
| T = 21 day | Test | $10^2$ | 12 | 16 | $1.4 \times 10^3$ |
| | PC | $10^7$ | 47 | 52 | $5 \times 10^8$ |
| | PCR | $10^3$ | 40 | 42 | $4.1 \times 10^4$ |
| T = 28 day | Test | $10^1$ | 27 | 26 | $2.7 \times 10^2$ |
| | PC | $10^7$ | 38 | 54 | $4.6 \times 10^8$ |
| | PCR | $10^3$ | 49 | 47 | $4.8 \times 10^4$ |

TABLE 21

NEUTRALIZER EFFICACY SCREEN
B. subtilis

| Time Interval | System Evaluated | Count A | Count B | Average |
|---|---|---|---|---|
| Day = 0 | Test | 60 | 54 | 57 |
| | PC | 51 | 68 | 60 |
| Day = 7 | Test | 92 | 104 | 98 |
| | PC | 91 | 98 | 95 |
| Day = 14 | Test | 25 | 25 | 25 |
| | PC | 14 | 16 | 15 |
| Day = 21 | Test | 14 | 21 | 18 |
| | PC | 21 | 21 | 21 |
| Day = 28 | Test | 51 | 50 | 51 |
| | PC | 45 | 38 | 42 |

EXAMPLE 2

A preservative effectiveness study was conducted using an aqueous solution of 0.1% by weight high purity benzyl alcohol (<100 ppm benzaldehyde), 0.5% trisodium edetate and 2.0% propylene glycol (the formula of Table 1 without Miranol 2 MCA Modified and Triton X-100).

The test system and preparation of the challenge organisms was the same as for Example 1 and the testing procedure was the same as Example 1 except that no rechallenge was performed.

The results of this study are presented in Table 7.

The concentration of S. aureus, P. aeruginosa and E. coli were reduced to at least 0.1% (three log values) of the initial concentration within the first fourteen (14) days. (Note: The initial concentration may be based upon the Positive Control T=0 Day concentration as a result of cidal action reducing the test sample T=0 Day concentration.) The concentration of viable C. albicans and A. niger remained at or below the initial concentration during the first fourteen (14) days.

The concentration of the positive controls were not reduced more than 10.0% (one log value).

Solution B as tested with S. aureus, P. aeruginosa, E. coli. C. albicans and A. niger meets the requirements of Preservative Efficacy after 14 days.

TABLE 22

| | Solution B | | | | |
|---|---|---|---|---|---|
| Organism | E. Coli ATCC 8739 | P. Aeruginosa ATCC 9027 | S. Aureus ATCC 6538 | A. Niger ATCC 16404 | C. Albicans ATCC 10231 |
| T = 0 | $1.7 \times 10^6$ | $9.8 \times 10^5$ | $3.1 \times 10^6$ | $5.0 \times 10^{3*}$ | $3.5 \times 10^5$ |
| Positive Control | $2. \times 10^6$ | $1.6 \times 10^6$ | $3.1 \times 10^6$ | $1.1 \times 10^5$ | $2.8 \times 10^5$ |
| T = 7 Days | <10 | $4.10^1$ | <10 | $2.5 \times 10^4$ | $7.8 \times 10^4$ |
| Positive Control | $2.1 \times 10^8$ | $1.5 \times 10^8$ | $2.1 \times 10^8$ | $4.5 \times 10^4$ | $1.3 \times 10^5$ |
| T = 14 Days | <10 | <10 | <10 | $2.8 \times 10^3$ | $9.2 \times 10^4$ |
| Positive Control | $4.1 \times 10^8$ | $1.0 \times 10^9$ | $4.2 \times 10^8$ | $1.2 \times 10^5$ | $4.4 \times 10^5$ |

*Note: For Test No. 1102, T = 0 A. Niger plates $10^2$ had approximately 50 colonies also clumped, difficult to enumerate. An initial level comparable to positive control was assumed.

The disclosures of U.S. Pat. Nos. 4,626,292, 4,543,200, 4,560,491 and 4,529,535 are hereby incorporated by reference.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A method of treating a contact lens comprising storing the lens during non-wearing periods in a non-abrasive aqueous cleaning solution comprising a disinfectant present in an effective amount for maintaining the sterility of the cleaning solution and for disinfecting the lens as a result of storage therein and a non-abrasive cleaning compound present in an effective amount for cleaning the lens, wherein said disinfectant comprises high purity benzyl alcohol.

2. The method of claim 1 wherein said disinfectant comprises a water soluble salt of ethylenediaminetetraacetic acid.

3. A method of treating a contact lens comprising:
   storing the lens during non-wearing periods in a non-abrasive aqueous cleaning solution comprising a disinfectant present in an effective amount for maintaining the sterility of the cleaning solution and for disinfecting the lens as a result of storage therein and a non-abrasive cleaning compound present in an effective amount for cleaning the lens; and
   wetting the lens after storage in said cleaning solution with a wetting solution comprising a wetting component and a preservative component wherein said preservative component of said wetting solution comprises high purity benzyl alcohol.

4. The method of claim 3 wherein said preservative component comprises a water soluble salt of ethylenediaminetetraacetic acid.

5. A cleaning, disinfecting, storing and wetting solution system for contact lenses comprising a nonabrasive sterile aqueous cleaning, conditioning and storing solution and a separate sterile aqueous wetting solution,
   (a) said sterile aqueous cleaning, disinfecting and storing solution for contact lenses comprising:
      (i) a hydrophilic disinfectant component consisting of effective amounts of high purity benzyl alcohol and a water soluble salt of ethylenediaminetetraacetic acid for maintaining the sterility of the cleaning, disinfecting and storing solution and for disinfecting contact lenses;
      (ii) at least one cleaning component present in an effective amount for cleaning the contact lens; and
      (iii) less than about one ppm by weight of benzaldehyde by total weight of said cleaning, disinfecting and storing solution; and
   (b) said sterile aqueous wetting solution comprising:
      (i) at least one wetting agent for contact lenses, present in an effective amount for wetting;
      (ii) a hydrophilic disinfectant component comprising effective amounts of high purity benzyl alcohol and a water soluble salt of ethylenediaminetetraacetic acid for maintaining the sterility of said wetting solution; and
      (iii) less than about one ppm by weight benzaldehyde by total weight of said wetting solution.

6. The system of claim 5 wherein said cleaning component comprises an alkylarylpolyether alcohol.

7. The system of claim 5 wherein said cleaning component comprises an amphoteric surface active agent.

8. The system of claim 5 wherein said wetting agent is selected from the group consisting of polyvinyl alcohol and polyvinylpyrrolidone.

9. The solution of claim 8 wherein said wetting agent is polyvinylpyrrolidone and polyvinyl alcohol.

10. The solution of claim 5 wherein said water soluble salt of ethylenediaminetetraacetic acid of said cleaning, conditioning and storing solution is trisodiumethylenediaminetetraacetic acid.

11. The system of claim 5 wherein said wetting solution has a pH in the range of from about 6.5 to 8.5 and a tonicity in the range of from about 0.91 to 1.65.

12. The system of claim 5 wherein said high purity benzyl alcohol has a benzaldehyde concentration of less than 100 ppm by weight of said benzyl alcohol.

13. The system of claim 5 wherein said cleaning, disinfecting and storage solution comprises, by weight of the total cleaning, conditioning and storage composition:
   from about 0.5% to about 20% 2-cocoyl-2-imidazolinium lauryl sulfate-1-carboxymethyloxyethyl-1-carboxymethyl disodium;
   from about 0.005% to about 5.0% isooctylphenoxypolyethoxyethane;
   from about 0.05% to about 1.0% benzyl alcohol; and
   from about 0.025% to about 0.5% trisodium edetate.

14. The system of claim 13 wherein said cleaning, conditioning and storage solution further comprises from about 0.005% to about 5.0% propylene glycol by weight of the total cleaning, disinfecting and storing composition.

15. A method of treating and caring for a rigid gas permeable contact lens with first and second nonabrasive aqueous solutions, comprising:
   (a) cleaning the rigid gas permeable lens with said first aqueous solution, which solution is a cleaning solution and consists of a disinfectant comprising high purity benzyl alcohol and a water soluble salt of EDTA, present in effective amounts for maintaining the sterility of said first solution and for disinfecting a contact lens as a result of storage therein, an alkylarylpolyether alcohol non-ionic detergent and an amphoteric surface active agent, present in effective amounts for cleaning the rigid gas permeable contact lens to allow wetting by said second aqueous solution and less than about one ppm benzaldehyde by total weight of the first aqueous solution; and thereafter
   (b) wetting the rigid gas permeable contact lens with said second aqueous solution that comprises a hydrophilic disinfectant system present in an effective amount for maintaining the sterility of said second solution and at least one wetting agent, present in an effective amount for wetting the lens, said disinfectant system consisting of high purity benzyl alcohol and a water soluble salt of ethylenediaminetetraacetic acid and less than about one ppm benzaldehyde by weight of the wetting solution.

16. The method of claim 15 further comprising storing the rigid gas permeable lens between wearing periods after said cleaning step in the cleaning solution to help disperse any contaminants remaining after cleaning.

17. The method of claim 15 wherein said wetting agent is selected from the group consisting of polyvinyl alcohol and polyvinylpyrrolidone.

18. The method of claim 15 wherein said water soluble salt of ethylenediaminetetraacetic acid of said cleaning solution is trisodiumethylenediaminetetraacetic acid.

19. The method of claim 15 wherein said alkylarylpolyether alcohol non-ionic detergent is an isooctylphenoxypolyethoxyethanol.

20. The method of claim 15 wherein said amphoteric surface active agent is 2-cocoyl-2-imidazolinium lauryl sulfate-1-carboxymethyloxyethyl-1-carboxymethyl disodium.

21. The method of claim 15 wherein said second aqueous solution comprises hydroxyethylcellulose and polyvinyl alcohol.

22. The method of claim 15 wherein said wetting solution has a pH in the range of from about 6.5 to 8.5 and a tonicity in the range of from about 0.91 to 1.65.

23. The method of claim 15 wherein said high purity benzyl alcohol has a benzaldehyde concentration of less than about 100 ppm by weight of said benzyl alcohol.

24. A method of caring for a contact lens comprising:
   (a) manually cleaning the contact lens with an aqueous non-abrasive cleaning solution containing at least one cleaning component for contact lenses; and
   (b) storing the contact lens in the aqueous non-abrasive cleaning solution during a non-wearing period.

25. The method of claim 24 further comprising rinsing the cleaning solution from the contact lens after the non-wearing period and wetting the contact lens with an aqueous wetting solution for the contact lens, the aqueous wetting solution comprising at least one wetting component suitable for wetting the contact lens.

26. The method of claim 24 wherein the cleaning component of the cleaning solution comprises a non-ionic detergent.

27. The method of claim 24 wherein the cleaning component of the cleaning solution comprises an amphoteric surface active agent.

28. A preserved ophthalmic drug solution comprising an aqueous ophthalmic drug solution and high purity benzyl alcohol, present in an effective amount for maintaining the sterility of the ophthalmic solution and the ophthalmic solution containing less than one ppm by weight of benzaldehyde by total weight of the ophthalmic solution.

29. The ophthalmic solution of claim 28 wherein high purity benzyl alcohol is present in an amount of from about 0.05% to about 1.0% by weight of the ophthalmic solution.

30. A non-abrasive cleaning, disinfecting and storing solution for contact lenses comprising:
(a) a hydrophilic disinfectant component consisting of effective amounts of high purity benzyl alcohol and a water soluble salt of ethylenediaminetetraacetic acid for maintaining the sterility of the cleaning, disinfecting and storing solution and for disinfecting contact lenses;
(b) at least one cleaning component present in an effective amount for cleaning the contact lens; and
(c) less than about one ppm by weight of benzaldehyde by total weight of said cleaning, disinfecting and storing solution.

31. The solution of claim 30 wherein said cleaning component comprises an alkylarylpolyether alcohol.

32. The solution of claim 30 wherein said cleaning component comprises an amphoteric surface active agent.

33. The solution of claim 30 wherein said water soluble salt of ethylenediaminetetraacetic acid of said cleaning, conditioning and storing solution is trisodiumethylenediaminetetraacetic acid.

34. The solution of claim 30 wherein said wetting solution has a pH in the range of from about 6.5 to 8.5 and a tonicity in the range of from about 0.91 to 1.65.

35. The solution of claim 30 wherein said high purity benzyl alcohol has a benzaldehyde concentration of less than 100 ppm by weight of said benzyl alcohol.

36. The system of claim 30 wherein said cleaning, disinfecting and storage solution comprises, by weight of the total cleaning, conditioning and storage composition:

from about 0.5% to about 20% 2-cocoyl-2-imidazolinium lauryl sulfate-1-carboxymethyloxyethyl-1-carboxymethyl disodium;
from about 0.005% to about 5.0% isooctylphenoxypolyethoxyethane;
from about 0.05% to about 1.0% benzyl alcohol; and
from about 0.025% to about 0.5% trisodium edetate.

37. The solution of claim 36 wherein said cleaning, conditioning and storage solution further comprises from about 0.005% to about 5.0% propylene glycol by weight of the total cleaning, disinfecting and storing composition.

38. A sterile aqueous contact lens wetting solution comprising:
(a) at least one wetting agent for contact lenses, present in an effective amount for wetting;
(b) a hydrophilic disinfectant component comprising effective amounts of high purity benzyl alcohol and a water soluble salt of ethylenediaminetetraacetic acid for maintaining the sterility of said wetting solution; and
(c) less than about one ppm by weight benzaldehyde by total weight of said wetting solution.

39. The system of claim 38 wherein said wetting agent is selected from the group consisting of polyvinyl alcohol and polyvinylpyrrolidone.

40. The solution of claim 38 wherein said water soluble salt of ethylenediaminetetraacetic acid of said wetting solution is trisodiumethylenediaminetetraacetic acid.

41. The solution of claim 38 wherein said wetting agent is polyvinylpyrrolidone and polyvinyl alcohol.

42. The system of claim 38 wherein said high purity benzyl alcohol has a benzaldehyde concentration of less than 100 ppm by weight of said benzyl alcohol.

43. A cold disinfecting aqueous solution especially suited for soft contact lenses comprising high purity benzyl alcohol and a water soluble salt of EDTA, present together in effective amounts for disinfecting a contact lens by storage therein.

44. The solution of claim 43 comprising from about 0.05% to about 1.0% high purity benzyl alcohol and from about 0.025 to about 0.75% salt of EDTA, all by weight of the total aqueous composition.

45. A composition for preserving the sterility of a contact lens solution comprising high purity benzyl alcohol having a benzaldehyde concentration of less than 100 ppm by weight of benzyl alcohol and a water soluble salt of EDTA.

* * * * *

UNITED STATES PATENT AND TRADEMARK OFFICE
CERTIFICATE OF CORRECTION

PATENT NO. : 5,322,667
DATED : June 21, 1994
INVENTOR(S) : Guy J. Sherman

It is certified that error appears in the above-indentified patent and that said Letters Patent is hereby corrected as shown below:

Title page, item [54] and col. 1, line 3,
In the Title, after "CLEANING" insert a comma --,--;
Item [56], Under References Cited, delete "4,406,706" and insert therefor --4,046,706-- and delete subclass "DIG. 7X" and insert therefor --DIG. 7XR--;
Col. 1, line 4, after "CLEANING" insert a comma --,--;
Col. 8, line 8, delete "sufficient" and insert therefor --sufficiently--;
Col. 12, line 25, delete "($Na_3PO_4.12H_2O$)" and insert therefor --($Na_3PO_4 \cdot 12H_2O$)--; line 27, delete "($NaH_2PO_4$).$H_2O$" and insert therefor --($NaH_2PO_4$)$\cdot H_2O$--;
Col. 14, line 7, after "*niger*" delete the period "." and insert therefor a comma --,--;
Col. 16, line 9, delete "$3.7 \times 10^7$" and insert therefor --$3.6 \times 10^7$--;
Col. 21, line 47, delete "system" and insert therefor --solution--.

Signed and Sealed this

Ninth Day of May, 1995

Attest:

BRUCE LEHMAN

*Attesting Officer*          *Commissioner of Patents and Trademarks*